United States Patent [19]

Everhardus et al.

[11] Patent Number: 4,629,671
[45] Date of Patent: Dec. 16, 1986

[54] CHARGE-TRANSPORTING COMPOUNDS AND PHOTOCONDUCTIVE ELEMENTS PROVIDED WITH SUCH CHARGE-TRANSPORTING COMPOUNDS

[75] Inventors: Roelof H. Everhardus, Lomm; Wilhelmus J. Bouts, Reuver; Johannes J. M. Brands, Arcen, all of Netherlands

[73] Assignee: Oce-Nederland B.V., Venlo, Netherlands

[21] Appl. No.: 762,925

[22] Filed: Aug. 6, 1985

[30] Foreign Application Priority Data

Sep. 5, 1984 [NL] Netherlands ................ 8402705

[51] Int. Cl.$^4$ ................................ G03G 5/14
[52] U.S. Cl. ........................... 430/59; 430/77
[58] Field of Search ................ 430/76, 77, 59

[56] References Cited

U.S. PATENT DOCUMENTS 4,403,025 9/1983 Horie et al. .............. 430/76 X
4,467,023 8/1984 Chu et al. ................ 430/59 X
4,500,619 2/1985 Ishikawa et al. .......... 430/77 X

FOREIGN PATENT DOCUMENTS 204054 12/1982 Japan .
90644 5/1983 Japan .

Primary Examiner—John D. Welsh
Attorney, Agent, or Firm—Reed Smith Shaw & McClay

[57] ABSTRACT

Charge-transporting compounds which form substantially colorless layers having a minimal residual charge and a good cleanability are disclosed. These compounds are of the general formula:

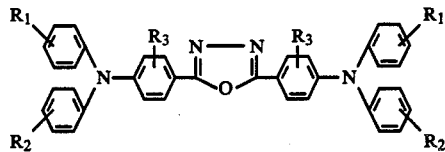

wherein R1, R2, and R3, individually, represent a hydrogen atom or an alkyl group containing 1 to 4 carbon atoms. Also disclosed is a photoconductive element containing a charge-generating compound and a charge-transporting compound of the general formula shown above which is homogeneously distributed in a binder. The charge-transporting compounds of the general formula are very soluble in various solvents and film-forming polymers providing for great maneuverability in processing the compounds into layers.

6 Claims, No Drawings

CHARGE-TRANSPORTING COMPOUNDS AND PHOTOCONDUCTIVE ELEMENTS PROVIDED WITH SUCH CHARGE-TRANSPORTING COMPOUNDS

BACKGROUND OF THE INVENTION

1. Field of the Invention

The present invention relates to charge-transporting compounds and to a photoconductive element comprising a support and one or more layers thereon containing at least a charge-generating compound and a charge-transporting compound which is homogeneously distributed in a binder.

2. Description of the Prior Art

Charge-transporting compounds and their use in photoconductive elements are generally disclosed in the prior art such as British Pat. No. 851,218 and its corresponding French counterpart, French Pat. No. 1,176,457. Typically, the charge-transporting compound is present together with a charge-generating compound in one layer on an electrically conductive support. Alternatively, a two-layer system can be used in which the charge-generating compound is provided in a charge-generating layer on the electrically conductive support and the charge-transporting compound is provided in a charge-transporting top layer as described in European Patent Application No. 0,085,447.

In the two-layer system of photoconductive elements, the charge-transporting top layer must meet stringent requirements with respect to the following ten properties: mechanical strength, uniformity and film forming ability, transparency to visible light, adhesiveness to the charge-generating layer, ability to act as a barrier for surface charge in the dark, charging value, hole-transporting or electron-transporting capacity, substantial absence of an injection barrier on the surface in contact with the charge-generating layer, good cleanability, and minimal residual charge after exposure.

Most known charge-transporting layers, however, have significant shortcomings with respect to one or more of the properties mentioned above. Currently, the charge-transporting layers which meet all of the above-mentioned properties most satisfactorily are those in which the charge-transporting compound is an azine selected from the group described in European Patent Application No. 0,085,447. Although excelllent photoconductive elements can be made with the azines disclosed in European Patent Application No. 0,085,447, there is a need for further improvement to meet even more stringent requirements with respect to the properties listed above.

SUMMARY OF THE INVENTION

Generally, the present invention provides new and improved charge-transporting compounds of the general formula:

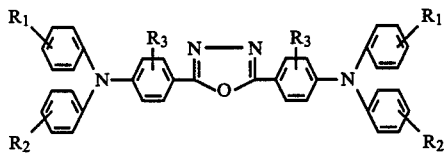

wherein R1, R2, and R3, individually, represent a hydrogen atom or an alkyl group containing 1 to 4 carbon atoms.

Charge-transporting compounds of the general formula are more satisfactorily soluble in various solvents and film-forming polymers than the azines. This reduces the risk of the crystallization phenomena occuring during layer formation and provides greater flexibility and maneuverability in processing the charge-transporting compound into layers. Moreover, high quality copies can be obtained with the charge-transporting compounds of the general formula even if partial charging occurs.

Further, the charge-transporting compounds described by the invention provide a photoconductive element which meets all of the stringent requirements of the above-mentioned properties, particularly the minimal residual charge, the good cleanability, and the substantial absence of an injection barrier on the surface in contact with the charge-generating layer. These ten properties are particularly important in photoconductive elements comprising a charge-transporting layer having a charge-transporting compound of the type described in this invention disposed on a thin charge-generating layer.

In two-layer systems having a charge-generating layer and a charge-transporting layer, the charge-generating compounds described by this invention have the additonal advantage that, as contrasted with yellow-colored azines, they form substantially colorless layers so that more light can penetrate into the underlying charge-generating layer. Thus, it is possible to achieve a much wider range of gain in photosensitivity depending on the light source used. Further, the resistance of photoconductive elements made from the charge-generating compounds of this invention to repeated use in the same electrophotographic process is somewhat higher than that of comparable elements having an azine charge-transporting compound as described in European Patent Application No. 0,085,447.

DESCRIPTION OF THE PREFERRED EMBODIMENTS

The present invention particularly provides a charge-transporting compound of the general formula shown above in which R1, R2, and R3 are preferably a hydrogen atom or a methyl group. The best results are obtained with 2,5-bis-(p-di-p-tolylamino-phenyl)-1,3,4-oxadiazole, a compound of the general formula wherein R1 and R2 each represent a methyl group in the para position and R3 represents a hydrogen atom.

The amount of charge-transporting compound described by the invention in the charge-transporting layer of the photoconductive element may vary within wide limits. It is generally between 15% by weight and 70% by weight, based on the weight of the total quantity of solid involved. The preferred amount is between 20% by weight and 40% by weight.

The insulating binder used in the charge-transporting layer of the photoconductive element described by the invention may be any material suitable for that purpose such as polystyrenes, silicone resins, polyesters of acrylic and methacrylic acid, vinyl polymers, and vinyl copolymers. Particularly good results are obtained when polycarbonates are used as the insulating binder because of their high transparency, mechanical strength, and good adhesion to the photoconductive layer.

The support used in the photoconductive element described by the invention may be any support known or used for that purpose. The support may be conductive itself, such as a support made of aluminum, steel, or nickel, or it may have been made conductive, such as a support made of paper or plastic to which a thin conductive layer of material, such as aluminum or nickel, has been applied.

The photoconductive element of the present invention is extremely suitable for use in indirect electrophotography because of its special properties. In indirect electrophotography, the ends of the support are generally interconnected making the support endless in form. Typical examples of endless supports are a drum or a flexible web of paper or plastics.

The radiation-sensitive, charge-generating compound used in the charge-generating layer of the photoconductive element described by the invention may be either inorganic or organic. Selenium and amorphous silicon are examples of inorganic charge-generating compounds. Preferably, however, organic compounds are used as the charge-generating compound. More particularly, the radiation-sensitive organic bis-azo compounds described in U.S. Pat. No. 4,052,210 are used as the charge-generating compound. The thickness of the photoconductive layer is preferably between about 0.2 and 2.0 microns.

In a preferred embodiment, the charge-transporting layer of the electrophotographic element described by the invention contains one or more activators. An activator is used to improve the discharge characteristics of the element. This is particularly important if in order to obtain a higher permanence the element is only partially charged, from 30% to 70% of its maximum chargeability (ASVmax). Any known activators for improving discharge characteristics may be used.

Examples of suitable activators are trinitrofluorenone, the dibenzothiophene oxides referred to in U.S. Pat. No. 3,905,814 and the N-(fluorene-9-ylidene)-anilines referred to in U.S. Pat. No. 3,935,009. Activators giving particularly good results were terephtala-dimalononitrile (hereafter "TDM") and 1,3,7-trinitro-dibenzothiophene-5,5-dioxide. For most activators, the amount required is generally between 1% and 15% by weight based on the charge-transporting agent. If, however, TDM is used in combination with a charge-transporting agent of the type described by the invention, the required results can be obtained with quantities between 0.5% and 3% by weight. Also, TDM, unlike many other activators, is absolutely non-mutagenic.

The electrophotographic element described by the invention can be made according to any of the processes described in the patent specifications referred to above. Both the preparation of the charge-generating layer and the charge-transporting layer are described in detail in these specifications. Charge-transporting compounds of the general formula can be prepared by reacting hydrazine in oleum with p-aminobenzoic acid, which may or may not be alkyl-substituted, and then reacting the resulting 2,5 bis-(p-aminophenyl)-1,3,4-oxadiazole with iodobenzene or alkyl iodobenzene in the presence of copper powder and potassium carbonate.

The latent image formed in the conventional way on the charge-transporting layer can be made visible either by means of a two-component developer or a one-component developer. A two-component developer, typically, consists of relatively coarse carrier particles, usually made of iron, and very finely divided toner particles which acquire the required polarity through contact with the carrier particles.

Typically, a one-component developer only consists of finely divided toner particles, which can be either conductive (resistivity less than $10^{10}$ Ohm.m) or insulating (resistivity greater than $10^{10}$ Ohm.m). The photoconductive element described by the invention has been found very suitable for producing a latent image which is then developed with a one-component developer. Use of a one-component developer has a number of advantages known to those skilled in the art.

When an insulating one-component developer is used, the photoconductive element described by the invention preferrably should be provided with a function layer in the form of a screen which produces a screen pattern in the image parts. Specific types of function layers and the place and method of their application are well-known to those versed in the art. For example, they are described in the book *Xeroxgraphy And Related Processes* by Dessauer and Clark, 1965, pp. 112–117.

When a conductive one-component developer is used, the photoconductive element described by the invention preferrably should be provided with a screen structure which, on image-wise exposure of the charged element, produces a charge screen pattern in the image background. A photoconductive element provided with a screen of this kind is described in Dutch Patent Application No. 84,00,922, which is not a prior publication.

The present invention will be explained in detail by reference to the following examples.

EXAMPLE 1

(a) Preparation of
2,5-bis-(p-amino-phenyl)-1,3,4-oxadiazole 60 g (0.46 mole) of hydrazine sulphate was dissolved in 700 ml of oleum with 20% $SO_3$. 137 g (1.0 mol) p-aminobenzoic acid was added at room temperature. The mixture was stirred for 2.5 hours at a temperature of 70° C. to 75° C. and then poured onto 10 liters of ice and neutralized with a concentrated sodium hydroxide solution. The resulting precipitate was filtered off, washed with water, and again filtered off. The yield was 91 g of impure product. This impure product was recrystallized in ethanol. After partial evaporation of the resulting liquid, 73.5 g of pure 2,5-bis-(p-aminophenyl)-1,3,4-oxadiazole were obtained.

(b) Preparation of
2,5-bis-(p-di-p-tolylaminophenyl)-1,3,4-oxadiazole

The following products were added to one another to form a mixture:
  40.8 g (0.16 mol) of 2,5-bis-(p-aminophenyl)-1,3,4-oxadiazole;
  157.8 g (0.72 mol) of p-iodotoluene;
  6.0 g copper powder;
  152.0 g anhydrous potassium carbonate; and
  400 ml nitrobenzene.

The mixture was refluxed at 210° C. for 7.5 hours with the continuous removal of water. The nitrobenzene was then removed by steam distillation and the residue extracted with toluene and reduced by evaporation. The solid obtained by evaporation (78 g) was recrystallized with 3.0 liters of ethyl acetate. After evaporation of the liquid to 500 ml, 54 g of pure 2,5-bis-(p-di-p-tolylamino-phenyl)-1,3,4-oxadiazole was filtered off.

EXAMPLE 2

A charge-generating layer containing the blue bis-azo dye 3,3'-dimethoxy-4,4'-bis(2"-hydroxy-3"-anilinecarbonyl naphthylazo)-biphenyl in molecularly divided form in a binder was prepared using the following steps.

A solution of 1.2 g of cellulose acetate butyrate in 60 ml of acetone was mixed with a solution of 1 g of 2-hydroxy-N-phenyl-3-naphtalene carboxamide in 13 ml of N,N-dimethylformamide. A solution of 0.5 g of 4,4'-bisdiazonium boron tetrafluoride salt of 3,3'-dimethoxybiphenyl in 7 ml of N,N-dimethyl formamide was added to this mixture. The resulting mixture was kept in the dark for 10 minutes and then applied to a conductive support (polyester film with a vapor-coated aluminum layer) by dip coating at 25° C. to 30° C. and 30% to 40% relative humidity. After drying, coupling to the above-mentioned bis-azo compound occurred in situ by treatment with ammonia. The thickness of the resulting charge-generating layer was 0.3 μm.

A charge-transporting layer was applied to the resulting charge-generating layer by dip coating with the following solution: 25 ml of 10% polycarbonate (Lexan-141 made by General Electric) in 1,2-dichloroethane (i.e. 2.5 g polycarbonate in 25 ml binder solution), 1.5 g of 2,5-bis(p-di-p-tolylamino-phenyl)-1,3,4-oxadiazole and 8 ml of tetrahydrofuran with 0.03 g of the activator terephthalaldimalonitrile dissolved therein. After drying in ambient air for 15 minutes, the resulting double layer was dried at 105° C. in a vacuum for 30 minutes.

Photocopies were made in an indirect photocopying machine using the resulting multi-layer electrophotographic element. The following properties were examined: layer thickness, layer adhesion strength, charging, dark discharge, photo-sensitivity, surface charge density, residual voltage, memory effect, permanence and copy image quality. The copy image quality was measured after developing the latent image on the charge-transporting layer with an electrically conductive one-component developer and then transferring it to ordinary paper and fixing it by heat and pressure. The results obtained with the electrophotographic element described in this example and the results obtained with the elements made according to Examples 3–9 are summarized after Example 9.

EXAMPLE 3

(Comparative Example)

Example 3 was the same as Example 2 except that the azine of 4-(di-4'-tolyl)aminobenzaldehyde was used as a charge-transporting compound instead of the oxadiazole of Example 2.

EXAMPLE 4

A charge-generating layer was prepared which contained the purple bis-azo dye 4,4'-bis(2"-hydroxy-3"-isopropylaminocarbonylnaphthylazo-)-stilbene in the form of small pigment particles (about 0.2 μm) as the charge-generating compound distributed in a binder. For this purpose, 1 g of the above-said bis-azo dye was dispersed in a solution of 1 g of cellulose acetate butyrate in 50 ml of 1,2-dichloroethane and 10 ml tetrahydrofuran by grinding for 24 hours in a ball mill. This preparation was applied by dip coating to a conductive support (polyester film with a vapor-coated aluminum layer). After drying, the thickness of this charge-generating layer was 1.0 μm.

A charge-transporting layer was applied to this charge-generating layer by dip coating with 2,5-bis-(-p-di-p-tolylaminophenyl)-1,3,4-oxadiazole, as described in Example 2.

EXAMPLE 5

(Comparative Example)

Example 5 was the same as Example 4 except that the azine compound of Example 3 was used as the charge-transporting compound instead of the oxadiazole of Example 2.

EXAMPLE 6

A charge-generating layer was prepared in which the purple bis-azo dye 4,4'-bis(2"-hydroxy-3"-isopropylamino-carbonylnaphthylazo)-stilbene and the red polycondensation product of p-phenylene-bisacetonitrile and 2,5 dimethoxy terephthalaldehyde (described in East German Pat. No. 75233) were the charge-generating compounds distributed in a binder as small pigment particles (about 0.2 μm).

For this purpose, 0.75 g of the above bis-azo dye and 0.75 g of the above polymeric dye after the addition of 15 ml of tetrahydrofuran were finely dispersed in a solution of 1.5 g of polyvinyl chloride-polyvinyl acetate copolymer (VMCH made by N. V. Contivema) in 60 ml of 1,2 dichloroethane by grinding for 72 hours in a ball mill.

This preparation was applied to a conductive support (polyester film with a vapor-coated aluminum layer) by dip coating. The thickness of the charge-generating layer after drying was 0.7 μm. A charge-transporting layer was then applied to the charge-generating layer by dip coating as described in Example 2 using the oxadiazole of Example 2.

EXAMPLE 7

(Comparative Example)

Example 7 is the same as Example 6 except that the azine compound of Example 3 was used in the charge-transporting layer instead of the oxadiazole of Example 2.

EXAMPLE 8

A charge-generating layer was prepared with the dark red pigment N,N'-dibenzyl-perylene-3,4;9,10-tetracarboxylic acid diimide as the charge-generating compound. A thin (0.2 μm) layer of the above-described perylene derivative was applied by vapor-coating to a conductive support (polyester film with a vapor-coated aluminum layer) at a pressure of $10^{15}$ to $10^6$ torr. A charge-transporting layer was applied to this charge-generating layer in the same manner as set forth in Example 2 using the oxadiazole of Example 2.

EXAMPLE 9

(Comparative Example)

Example 9 is the same as Example 8 except that the azine compound of Example 3 was used in the charge-transporting layer instead of the oxadiazole of Example 2.

RESULTS OF EXAMPLES 2–9

In Examples 3, 5, 7, and 9, the hot preparation containing the dissolved charge-transporting azine has to be processed rapidly to avoid crystallizing it out either in the solution or on the layer. In Examples 2, 4, 6, and 8, the charge-transporting oxadiazole remains completely in solution at room temperature.

The charge-transporting layers from the examples were about 4 μm thick. The adhesion strength of the layers was excellent. In every case, upon partial charging, the memory effect was in every case totally absent. The copy quality using a one-component developer of the layers made as described in Examples 2, 4, 6, and 8 was excellent both with complete and partial charging, as was the quality of the layers made as described in Examples 3, 5, 7, and 9 (the comparative examples). All the layers were easily cleaned using a one-component developer.

The photoelectric results at complete charging are summarized in Table 1 while the results for partial charging are given in Table 2.

TABLE 1

| | Maximum Charging | | | | | |
|---|---|---|---|---|---|---|
| Example | ASV (volts) | D.O.-1 (%) | D.O.-5 (%) | sigma (mC/m$^2$) | L-20 (mJ/m$^2$) | Residual (%) |
| 2 | 410 | 9 | 21 | 3.3 | 39 | 5 |
| 3 (comparative example) | 420 | 9 | 20 | 3.3 | 40 | 3 |
| 4 | 628 | 7 | 17 | 3.5 | 30 | 7 |
| 5 (comparative example) | 657 | 7 | 15 | 3.1 | 34 | 5 |
| 6 | 415 | 11 | 24 | 2.4 | 18 | 4 |
| 7 (comparative example) | 479 | 14 | 30 | 2.1 | 20 | 3 |
| 8 | 495 | 4 | 12 | 3.7 | 22 | 2 |
| 9 (comparative example) | 423 | 12 | 31 | 2.8 | 23 | 1 |

TABLE 2

| | Partial Charging | | | | | |
|---|---|---|---|---|---|---|
| Example | ASV (volts) | D.O.-1 (%) | D.O.-5 (%) | sigma (mC/m$^2$) | L-20 (mJ/m$^2$) | Residual (%) |
| 2 | 197 | 2 | 8 | 1.8 | 40 | 9 |
| 3 (comparative example) | 198 | 2 | 8 | 1.7 | 40 | 5 |
| 4 | 222 | 4 | 11 | 1.4 | 27 | 8 |
| 5 (comparative example) | 219 | 5 | 15 | 1.0 | 28 | 5 |
| 6 | 229 | 7 | 18 | 1.4 | 17 | 6 |
| 7 (comparative example) | 205 | 10 | 25 | 1.1 | 18 | 5 |
| 8 | 201 | 1 | 2 | 1.6 | 13 | 2 |
| 9 (comparative example) | 200 | 2 | 5 | 1.6 | 15 | 1 |

Where:
ASV=surface potential in volts after charging;
D.O.−1 and D.O.−5=dark discharge in 1 and 5 seconds, respectively, after charging as a percent of the ASV;
Sigma=surface charge density in mC/m$^2$, measured after 1 second dark discharge;
L-20=amount of light in mJ/m$^2$ to discharge the layer to 20% of the ASV using a flash (BRAUN flash type F900);
Residual=percentage of the ASV remaining after exposure with 100 mJ/m$^2$ of light (BRAUN flash type F900).

EXAMPLE 10

The charge-transporting layer containing 2,5-bis(p-di-p-tolylaminophenyl)-1,3,4 oxadiazole has a high transparency to short-wave light which results in greater photosensitivity and color reproduction than the charge-transporting layer containing the yellow azine of 4-(di-4′-tolyl)aminobenzaldehyde. To compare the differences, the photoconductive elements from Examples 8 and 9 were exposed through different narrow band filters after charging. The photoelectric results using filters with transmission maxima of from 411 to 526 nm, respectively, are given in Table 3. At wavelengths higher than those given in Table 3, the layers of both examples behave identically. The symbols in Table 3 are defined in the same way as in Tables 1 and 2.

TABLE 3

In both cases ASV = 210 Volts; sigma = 1.6 mc/m$^2$;
D.O.-1 Example 8 = 1%; D.O.-1 Example 9 = 2%

| Wavelength (nm) | L-20 (Example 8) (mJ/m$^2$) | L-20 (Example 9) (mJ/m$^2$) |
|---|---|---|
| 411 | >100 | >>100 |
| 435 | 17 | >100 |
| 463 | 8 | >100 |
| 476 | 8 | 20 |
| 488 | 8 | 9 |
| 501 | 7 | 7 |
| 526 | 7 | 7 |

While presently preferred embodiments of the invention have been described in particularity, the invention may be otherwise embodied within the scope of the appended claims.

What is claimed is:

1. A photoconductive element comprising a support and one or more layers, containing together a "transparent and substantially colorless" charge-generating compound and a charge-transporting compound which is homogeneously distributed in a binder, wherein the charge-transporting compound is of the general formula:

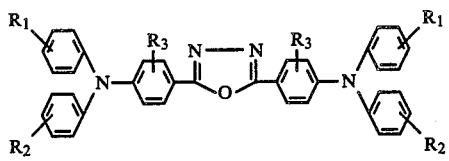

wherein R1, R2, and R3, individually, represent a hydrogen atom or an alkyl group containing 1 to 4 carbon atoms.

2. A photoconductive element as described in claim 1, wherein R1, R2, R3, individually, represent a hydrogen atom or a methyl group.

3. A photoconductive element as described in claim 1, wherein R1 and R2, individually, represent a methyl group in the para position and R3 represents a hydrogen atom.

4. A photoconductive element comprising a support, a charge-generating layer containing a charge-generating compound and a transparent and substantially colorless charge-transporting layer containing a charge-transporting compound which is homogeneously distributed in a binder, wherein the charge-transporting compound is of the general formula:

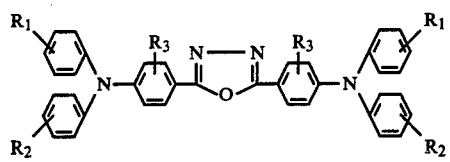

wherein R1, R2 and R3, individually, represent a hydrogen atom or an alkyl group containing 1 to 4 carbon atoms.

5. A photoconductive element as described in claim 4, wherein R1, R2 and R3, individually, represent a hydrogen atom or a methyl group.

6. A photoconductive element as described in claim 5, wherein R1 and R2, individually, represent a methyl group in the para position and R3 represents a hydrogen atom.

* * * * *